(12) United States Patent
Serrano et al.

(10) Patent No.: US 8,187,194 B2
(45) Date of Patent: May 29, 2012

(54) METHOD OF MOUNTING A TRANSDUCER TO A DRIVESHAFT

(75) Inventors: Manuel Serrano, Menlo Park, CA (US); James D. Koger, Santa Cruz, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 12/793,115

(22) Filed: Jun. 3, 2010

(65) Prior Publication Data

US 2010/0274140 A1 Oct. 28, 2010

Related U.S. Application Data

(62) Division of application No. 10/299,315, filed on Nov. 18, 2002, now Pat. No. 7,762,955, which is a division of application No. 09/755,873, filed on Jan. 4, 2001, now abandoned.

(51) Int. Cl.
*A61B 8/00* (2006.01)

(52) U.S. Cl. .......................... 600/466; 600/459; 600/463

(58) Field of Classification Search .................... 600/466
See application file for complete search history.

(56) References Cited

U.S. PATENT DOCUMENTS

| | | | |
|---|---|---|---|
| 3,552,630 A * | 1/1971 | Dean | 228/46 |
| 4,070,077 A * | 1/1978 | Clark | 439/876 |
| 4,170,897 A | 10/1979 | Babcock | |
| 4,276,491 A | 6/1981 | Daniel | |
| 4,576,177 A | 3/1986 | Webster | |
| 4,951,677 A | 8/1990 | Crowley et al. | |
| 5,243,988 A | 9/1993 | Sieben et al. | |
| 5,313,957 A | 5/1994 | Little | |
| 5,361,768 A | 11/1994 | Webler et al. | |
| 5,368,035 A | 11/1994 | Hamm et al. | |
| 5,372,138 A | 12/1994 | Crowley et al. | |
| 5,377,685 A | 1/1995 | Kazi et al. | |
| 5,437,282 A | 8/1995 | Koger et al. | |
| 5,503,154 A | 4/1996 | Belef | |
| 5,520,189 A | 5/1996 | Malinowski et al. | |
| 5,606,975 A | 3/1997 | Liang et al. | |
| 5,682,897 A | 11/1997 | Pomeranz | |
| 5,699,805 A | 12/1997 | Seward et al. | |
| 5,738,100 A | 4/1998 | Yagami et al. | |
| 5,842,994 A | 12/1998 | TenHoff et al. | |
| 5,951,480 A | 9/1999 | White et al. | |
| 6,004,269 A * | 12/1999 | Crowley et al. | 600/439 |
| 6,019,726 A | 2/2000 | Webb | |
| 6,106,474 A | 8/2000 | Koger et al. | |
| 6,120,454 A | 9/2000 | Suorsa et al. | |

(Continued)

OTHER PUBLICATIONS

U.S. Appl. No. 10/299,315, Official Communication mailed May 8, 2003; 10 pgs.

(Continued)

*Primary Examiner* — Jonathan Cwern

(74) *Attorney, Agent, or Firm* — Frommer Lawrence & Haug LLP; Bruce E. Black

(57) ABSTRACT

A method of mounting a transducer to a driveshaft which eliminates the need for a transducer housing, the improved method directly attaches the transducer to a rigid distal tip of a driveshaft which is part of a rotatable imaging core of a catheter assembly. The method contemplates heat treating the distal tip of the driveshaft to make it rigid, machining the distal tip to be dimensioned to hold the transducer, and attaching the transducer to the distal tip by clamping, crimping, or an adhesive.

21 Claims, 3 Drawing Sheets

U.S. PATENT DOCUMENTS

| | | | |
|---|---|---|---|
| 6,125,037 A * | 9/2000 | Bollesen | 361/704 |
| 6,166,998 A | 12/2000 | Hare | |
| 6,241,703 B1 * | 6/2001 | Levin et al. | 604/22 |
| 6,248,076 B1 | 6/2001 | White et al. | |
| 6,471,653 B1 | 10/2002 | Jordfald et al. | |
| 6,599,288 B2 | 7/2003 | Maguire et al. | |
| 2002/0087080 A1 | 7/2002 | Slayton et al. | |

OTHER PUBLICATIONS

U.S. Appl. No. 10/299,315, Official Communication mailed Oct. 28, 2003; 6 pgs.

U.S. Appl. No. 10/299,315, Official Communication mailed May 21, 2004; 4 pgs.

U.S. Appl. No. 10/299,315, Official Communication mailed Oct. 15, 2004; 7 pgs.

U,S. Appl. No. 10/299,315, Official Communication mailed May 6, 2005; 5 pgs.

U.S. Appl. No. 10/299,315, Official Communication mailed Dec. 21, 2005; 7 pgs.

U.S. Appl. No. 10/299,315, Official Communication mailed Aug. 10, 2006; 6 pgs.

U.S. Appl. No. 10/299,315, Official Communication mailed Mar. 6, 2008; 10 pgs.

U.S. Appl. No. 10/299,315, Official Communication mailed Sep. 11, 2008; 9 pgs.

U.S. Appl. No. 10/299,315, Official Communication mailed Jul. 13, 2009; 11 pgs.

U.S. Appl. No. 10/299,315, Official Communication mailed Dec. 29, 2009; 8 pgs.

U.S. Appl. No. 10/299,315, Notice of Allowance mailed Mar. 19, 2010.

* cited by examiner

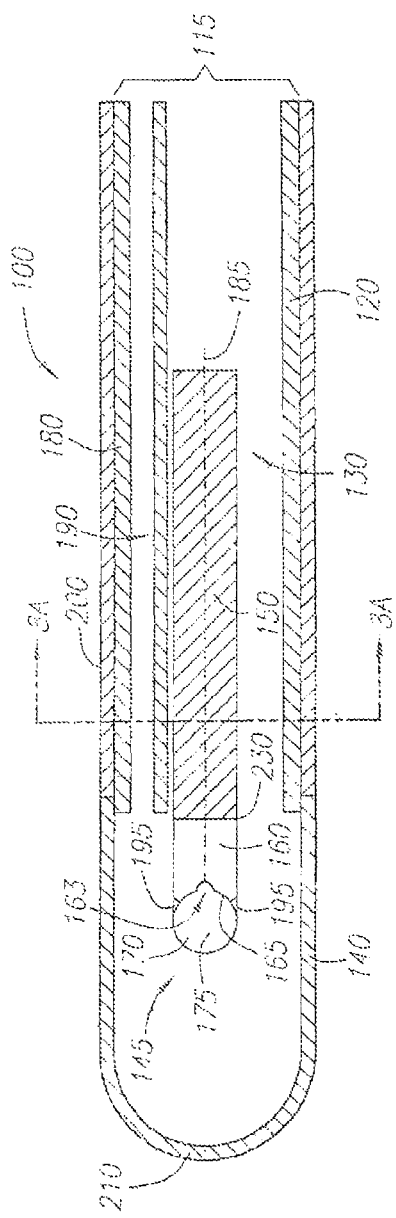
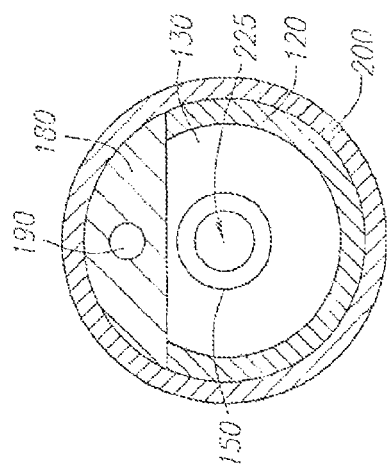
FIG. 3
FIG. 3A

METHOD OF MOUNTING A TRANSDUCER TO A DRIVESHAFT

PRIOR APPLICATIONS

This application is a divisional of U.S. Patent Application Ser. No. 10/299,315, filed on Nov. 18, 2002, now U,S. Pat. No. 7,762,955, which is a divisional of U.S. Patent Application Ser. No. 09/755,873, filed on Jan. 4, 2001, abandoned.

FIELD OF THE INVENTION

The present invention relates, in general, to transducer mountings for ultrasound catheter assemblies used in diagnostic or therapeutic applications.

DISCUSSION OF RELATED ART

Mechanically scanned ultrasound catheter assemblies employ a single transducer mounted inside a rotating housing. In particular, the transducer transmits and receives ultrasonic waves while the transducer housing rotates about a fixed axis in an acoustic window located at a distal tip of the catheter. The rotational motion of the transducer housing is accomplished by a flexible driveshaft that extends through an axially disposed lumen of the catheter, wherein the driveshaft has one end connected to the transducer housing. Once the distal end of the catheter is positioned, for example, in a patient's vascular system, a cross-sectional image of the tissue surrounding the distal catheter tip is produced by using imaging and control circuitry that are electrically coupled to the transducer via an electrical conductor extending through the drive shaft.

With respect to FIG. 1, a conventional prior art ultrasound catheter assembly 100, which appears in U.S. Pat. No. 5,842,994, is depicted. U.S. Pat. No. 5,842,994 is hereby incorporated by reference. The catheter assembly 100 comprises a first elongate tubular element 120, which forms an axially disposed lumen 130. An acoustic imaging window 140 is attached to a distal end of the first tubular element 120, thereby forming an enclosed tip of the catheter assembly 100. A flexible driveshaft 150 extends through the lumen 130 and is connected at a distal end to a transducer housing 60 disposed in the acoustic imaging window 140. The transducer housing 60 has a generally cylindrical transducer 170 mounted therein, exposing a circular active surface area, or aperture. A second elongate tubular element 180 forms an additional lumen 190 used for other catheter functions such as housing pullwires or delivering liquid to a distally disposed balloon during angioplasty.

With further reference to FIG. 1, the transducer housing 60 is an expensive, high-precision part that requires a particular joining operation to attach it to the driveshaft 150. In addition, the joint created between the driveshaft 150 and the transducer housing 60 may potentially fail. Therefore, it would be advantageous to eliminate the transducer housing 60 from catheter assembly 100. FIG. 1A depicts an alternative conventional prior art ultrasound catheter, which includes opening 65 adapted to permit flushing from the proximal end of catheter assembly 100 and, if a separate lumen is provided, dimensioned for the passage of guide wires. This alternative catheter does not include first elongate tubular element 120 or second elongate tubular element 180.

SUMMARY OF THE INVENTION

An aspect of the invention involves a method of making a transducer mounting to a driveshaft by providing an elongate tubular element including a lumen, providing a rotatable imaging core adapted to pass through the lumen, the imaging core including a flexible driveshaft and a transducer. The method optionally contemplates treating and machining the distal tip of the driveshaft, and then attaching the transducer to the distal tip.

Another separate aspect of the invention involves a method of making a transducer mounting to a driveshaft comprising a step of treating the distal tip of the driveshaft by hardening the distal tip with a welding process, wherein the driveshaft is initially made of flexible wound wires and the welding process joins the wound wires of the distal tip together such that a rigid distal tip is formed. This method optionally contemplates the use of electrical welding by applying electrodes at two locations on the drive shaft for electrical conductivity therebetween.

A further separate aspect of the invention involves a method of making a transducer mounting to a driveshaft comprising a step of treating the distal tip of the driveshaft by hardening the distal tip with a soldering process, wherein the driveshaft is made of flexible wound wires having interstices therebetween and the soldering process fills the interstitial spaces such that a rigid distal tip is formed. This method optionally contemplates the use of a cold clamp having a high specific heat to dissipate excess heat during soldering. In addition, this method may incorporate the use of a ceramic or fiber-optic plug for keeping the central lumen open during soldering.

An additional separate aspect of the invention involves a method of making a transducer mounting to a driveshaft comprising a step of machining the distal tip of the driveshaft by grinding or drilling the distal tip to form an arcuate recession with opposing tapered side walls. This method optionally contemplates attaching the transducer to the distal tip of the driveshaft by crimping the tapered side walls about the perimeter of the transducer so that the transducer is held in place therebetween. In addition, a clamping member or an adhesive may be used to secure the transducer to the distal tip of the drive shaft.

Yet another separate aspect of the invention involves an ultrasonic imaging catheter assembly comprising an elongate tubular element including a lumen, a rotatable imaging core adapted to pass through the lumen, the rotatable imaging core including a flexible driveshaft attached to a transducer, wherein the driveshaft has a rigid distal tip adapted to be mounted to the transducer.

An additional separate aspect of the invention involves an ultrasonic imaging catheter assembly having a driveshaft with a rigid distal tip which includes an arcuate recession with opposing tapered side walls, wherein the transducer is attached to the distal tip of the driveshaft by crimping the tapered side walls about the perimeter of the transducer so that the transducer is held in place therebetween. Alternatively, a clamping member or an adhesive may be used to secure the transducer to the distal tip of the drive shaft.

The invention may include any one of these separate aspects individually, or any combination of these separate aspects.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

FIG. 3 is a cut-away partial side view of the ultrasound catheter assembly of FIG. 2.

FIG. 3A is a cross-sectional view taken along line 3A-3A of FIG. 3.

DETAILED DESCRIPTION OF THE PREFERRED EMBODIMENT

Figure 2:
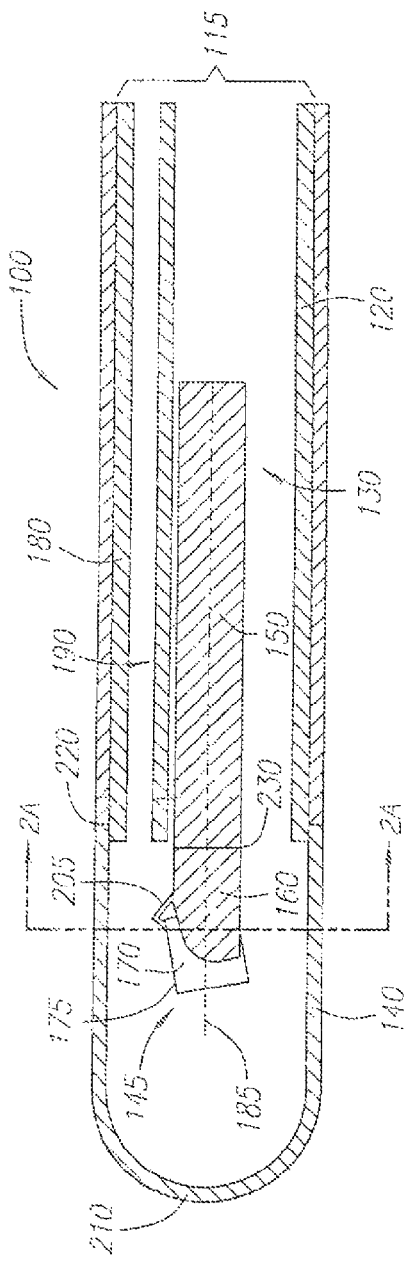
FIG. 2 is a cut-away partial side view of an ultrasound catheter assembly according to an example embodiment of the present invention.

With respect to FIGS. 2 and 3, a preferred ultrasound catheter assembly 100 includes an elongate tubular element 115 having tubular section 120, which forms an axially disposed lumen 130. A dome-shaped acoustic imaging window 140 is attached to a distal end of the elongate tubular element 115, thereby forming an enclosed tip of the catheter assembly 100. Alternatively, the shape of the acoustic imaging window 140 may be virtually any shape or combination of shapes. An imaging core 145 comprising a flexible driveshaft 150 having a rigid distal tip 160 and a generally cylindrical transducer 170 is disposed within lumen 130. The imaging core 145 is capable of translation along its center axis 185.

Figure 2A:
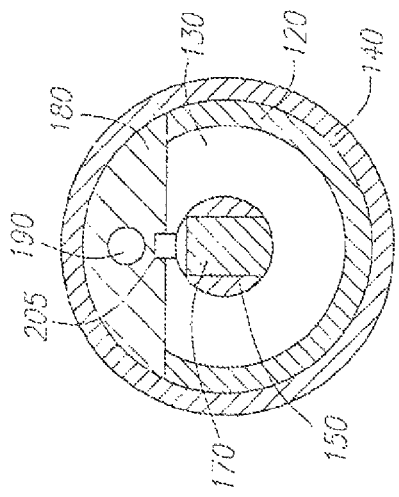
FIG. 2A is a cross-sectional view taken along line 2A-2A of FIG. 2.

As best seen in FIG. 2A, axially disposed lumen 130 has a substantially "D-shaped" cross-section wherein the inner dimensions of lumen 130 are sufficient for transducer 170 to be translated therein. With further reference to FIG. 2A, a solid section 180 of elongate tubular element 115 forms an additional lumen 190 used for other catheter functions such as, by way of non-limiting examples, housing pullwires, drug delivery, balloon angioplasty, laser ablation, or for housing a stiffening member to help prevent the collapsing of the catheter assembly.

A cover tube 200 (FIG. 3) formed of a suitable material, such as a heat shrinkable nylon, urethane, polyethylene or other plastic, is disposed around tubular element 115, wherein cover tube 200 provides both structural integrity to the catheter assembly 100, as well as a smooth outer surface for ease in axial movement in a patient's body passage with minimal friction. Preferably, the acoustic imaging window 140 has its proximal end open and its distal end rounded and is attached to a distal outer circumferential portion of the tubular element 115 to form an enclosed catheter tip 210, with respective ends of the cover tube 200 and acoustic imaging window 140 bonded together at a common joint 220. The outer diameter of the proximal end of window 140 is preferably substantially equal to that of the installed cover tube 200, so that a smooth outer surface is provided at joint 220.

Referring to FIGS. 2 and 3, the transducer 170 is attached to the flexible driveshaft 150 at a cut-away portion 165 (FIG. 3) of rigid distal tip 160 such that its active surface 175 slopes at a slight angle with respect to the center axis 185 of driveshaft 150. This tilting of transducer 170 helps to minimize internal reflections inside of catheter tip 210. The transducer 170 can be fixedly attached in a number of ways including by an adhesive such as a UV (ultraviolet light) cure epoxy, by crimping of opposing tapered side walls 195 surrounding cut-away portion 165, by a clamp 205, any other known method of affixing, or any combination of these methods.

As best seen in FIGS. 3 and 3A, driveshaft 150 has a central lumen 225 adapted for the passage of transducer wires or coaxial cable, which extend through relieved area 163. The driveshaft 150 is made of wound wire such as a super alloy or stainless steel in order to be flexible inside of a patient's blood vessel, for example. However, distal tip 160 of driveshaft 150 preferably should be hardened and machined in order to mount transducer 170. Hardening of distal tip 160 can be accomplished by a number of means including welding and soldering.

Welding of the distal tip 160 is preferably accomplished electrically, by applying electrodes at two locations along distal tip 160 for conductivity therebetween. The two locations can be the end of distal tip 160 and, for example, location 230 along the driveshaft 150. By running sufficient electricity between these two locations, the wound wires of driveshaft 150 will heat up, begin to liquefy, and bond together, eliminating some of the interstitial spaces between the wound wires. Although electrical welding of the distal tip 160 should be continued until the wires have fused together, it should be terminated before unwanted deformation of the distal tip 160 has occurred. After welding and a brief cool-down period, the distal tip 160 will be more rigid than the rest of the driveshaft 150 due to the fusing between the wound wires.

Alternatively, the hardening of the distal tip 160 can be accomplished by a soldering process wherein the interstitial spaces between the wound wires are filled with softened metal. Although many different solders can be used, the solder is preferably a 5% silver solder mixed with 95% tin. During the soldering process, the silver solder should be heated to approximately 850-900 degrees Fahrenheit and melted into the interstitial spaces in the distal tip 160 of driveshaft 150. Alternatively, a brazing process can be used, which requires greater temperatures to melt solder having a higher percentage of silver.

During soldering, a cold clamp can be utilized to dissipate excess heat and to limit unnecessary fusion of the wound wires of the rest of the flexible driveshaft 150. Ideally, the cold clamp is made of metal such as aluminum or copper having a high specific heat. Also, the cold clamp is circular so that it can encircle the perimeter of drive shaft 150 at location 230. Before soldering, a plug should be inserted within central lumen 225 so that it is not stopped up by melted metal. Preferably, the plug is made of a material having a high melting point such as a ceramic rod or a piece of fiber optic. In addition, the plug can have an outer coating to prevent adherence to the solder.

The hardening of the distal tip may also be accomplished using an adhesive such as an epoxy wherein an adhesive is used to fill the interstitial spaces of the wound wire of distal tip 160. After the distal tip 160 has been hardened so that it is rigid, it can be machined to create an effective mount for transducer 170.

During machining, a cut-away portion 165 in the form of an arcuate recession with opposing tapered side walls 195 is formed on the rigid distal tip 160 using a milling or grinding process. In addition, relieved area 163 is formed within cut-away portion 165 using a similar milling or grinding process. Cut-away portion 165 is adapted to receive the cylindrical transducer 170. The opposing tapered walls 195 of machined distal tip 160 can be crimped inwardly about the perimeter of the transducer 170 to hold it fixedly in place. Additionally, an epoxy or other adhesive such as a UV cure epoxy can be used to further secure transducer 170 to distal tip 160. Alternatively, clamping member 205 can be used to secure the transducer 170 to the distal tip 160 of the driveshaft 150. The clamping member is fixedly attached to the driveshaft 150 and removably attached to the transducer 170.

Figure 1:
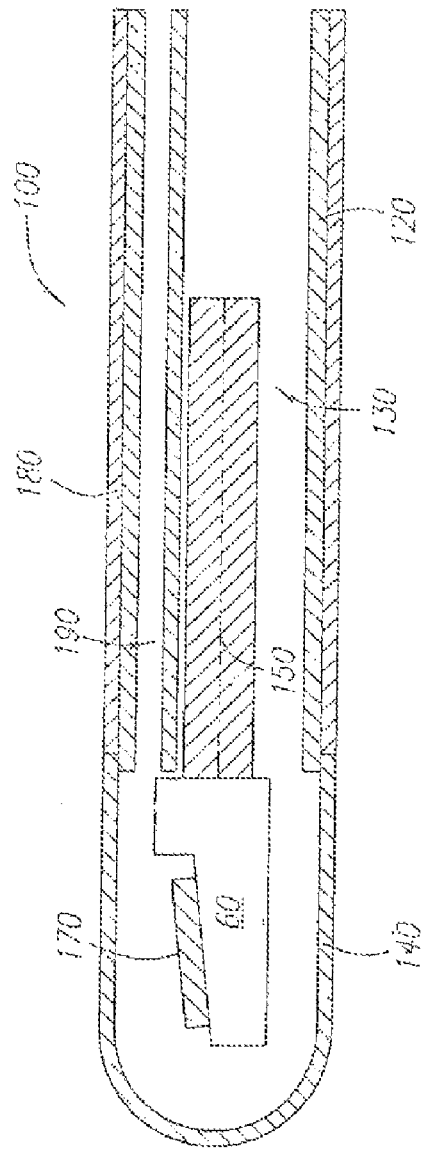
FIG. 1 is a cut-away partial side view of a prior art ultrasound catheter assembly.
Figure 1A:
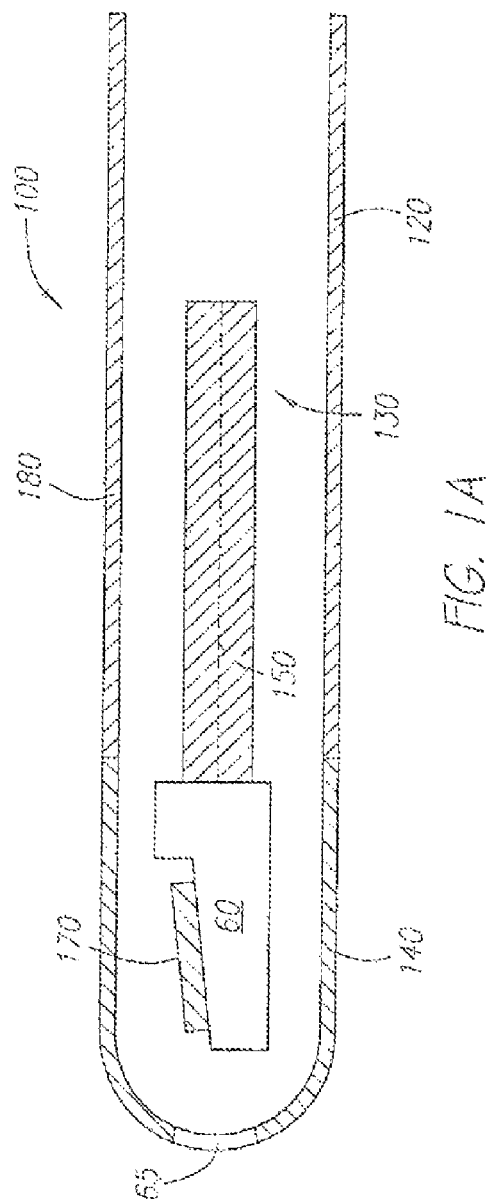
FIG. 1A is a cut-away partial side view of a prior art ultrasound catheter assembly.

Any one or more of the features depicted in FIGS. 1-3, or described in the accompanying text, may be interchanged with that of another figure to form still other embodiments.

While preferred embodiments and methods have been shown and described, it will be apparent to one of ordinary skill in the art that numerous alterations may be made without departing from the spirit or scope of the invention. Therefore, the invention is riot limited except in accordance with the following claims.

The invention claimed is:

1. An ultrasonic imaging catheter assembly comprising:
an elongate tubular element including a lumen;
a rotatable imaging core adapted to pass through the lumen, the rotatable imaging core including a flexible driveshaft, the driveshaft comprising a plurality of wires wound together and having interstices therebetween, the wires forming a rigid distal tip machined such that a transducer is attachable thereon; and
the transducer disposed, without a transducer housing, directly onto the wires forming the distal tip of the driveshaft.

2. The ultrasonic imaging catheter assembly of claim 1 wherein the wires in the rigid distal tip are joined together.

3. The ultrasonic imaging catheter assembly of claim 1 further comprising a softened metal located in the interstices of the rigid distal tip.

4. The ultrasonic imaging catheter assembly of claim 1 further comprising an adhesive located in the interstices of the rigid distal tip.

5. The ultrasonic imaging catheter assembly of claim 1 wherein the rigid distal tip comprises crimped side walls about the perimeter of the transducer, wherein the crimped sidewalls hold the transducer therebetween.

6. The ultrasonic imaging catheter assembly of claim 1 wherein the transducer is removably attached to the driveshaft with a clamping member.

7. The ultrasonic imaging catheter assembly of claim 1 wherein the transducer is attached to the distal tip with an adhesive.

8. The ultrasonic imaging catheter assembly of claim 1 further comprising a generally cylindrical imaging window.

9. The ultrasonic imaging catheter assembly of claim 1 wherein the transducer has a circular surface.

10. The ultrasonic imaging catheter assembly of claim 1 wherein the elongate tubular element further includes a second lumen.

11. The ultrasonic imaging catheter assembly of claim 10 wherein the second lumen is adapted to house a steering pullwire.

12. A catheter assembly comprising:
an elongate tubular element including a lumen;
a rotatable imaging core adapted to pass through the lumen, the rotatable imaging core including a flexible driveshaft having a distal tip;
the flexible driveshaft comprising a plurality of wires wound together and having interstices therebetween and forming an arcuate recession with opposing tapered side walls, wherein at least one interstice at the distal tip is filled with solder, the wires and solder at the distal tip being configured and arranged for placement of an ultrasound transducer directly onto the wires and solder and within the arcuate recession; and
the ultrasound transducer disposed, without a transducer housing, directly onto the wires forming the distal tip of the driveshaft.

13. The catheter assembly of claim 12 further comprising a cold clamp clamped to the driveshaft, the cold clamp having a high specific heat.

14. The catheter assembly of claim of claim 13 wherein the cold clamp is made of aluminum.

15. The catheter assembly of claim 13 wherein the cold clamp is made of copper.

16. The catheter assembly of claim 12 wherein the wires define a driveshaft lumen located within the driveshaft.

17. The catheter assembly of claim 16 further comprising a plug located within the driveshaft lumen to prevent solder in the distal tip from plugging the driveshaft lumen.

18. The catheter assembly of claim 17 wherein the plug is ceramic.

19. The catheter assembly of claim 17 wherein the plug includes a piece of fiber-optic.

20. The catheter assembly of claim 12 wherein the elongate tubular element further includes a second lumen.

21. The catheter assembly of claim 20 wherein the second lumen is adapted to house a steering pullwire.

* * * * *